United States Patent [19]

Turnell et al.

[11] Patent Number: 4,837,157
[45] Date of Patent: Jun. 6, 1989

[54] SAMPLE PREPARATION METHOD FOR LIQUID CHROMATOGRAPHY

[75] Inventors: David C. Turnell, Balsall Common; John D. H. Cooper, Sapcote, both of England

[73] Assignee: Coventry Health Authority, Coventry, United Kingdom

[21] Appl. No.: 917,291

[22] Filed: Oct. 8, 1986

Related U.S. Application Data

[63] Continuation of Ser. No. 515,499, Jul. 20, 1983, abandoned.

[30] Foreign Application Priority Data

Jul. 20, 1982 [GB] United Kingdom ............... 8220963

[51] Int. Cl.$^4$ .................. G01N 1/28; G01N 30/08; G01N 30/14; G01N 33/02
[52] U.S. Cl. ............................. 436/20; 73/61.1 C; 210/198.2; 210/260; 210/321.71; 210/321.72; 210/321.75; 210/656; 210/659; 422/70; 436/89; 436/98; 436/161; 436/178; 436/179
[58] Field of Search .................. 55/16, 67, 158; 73/864.12, 864.22, 61.1 C; 127/54; 210/254, 259, 260, 295, 321.1, 321.3, 282, 198.2, 656, 659; 422/70, 100, 101; 436/54, 161, 177–179, 20, 89, 90, 98

[56] References Cited

U.S. PATENT DOCUMENTS

| | | | |
|---|---|---|---|
| 4,824 | 10/1846 | Read ........................... | 210/453 X |
| 2,502,614 | 4/1950 | Zender ........................ | 127/54 |
| 2,789,654 | 4/1957 | Zurit ........................... | 210/282 X |
| 3,211,645 | 10/1965 | Ferrari ........................ | 210/321.2 X |
| 3,352,644 | 11/1967 | Lysyj ........................... | 436/161 |
| 3,572,994 | 3/1971 | Hochstrasser ............... | 210/321.2 X |
| 3,625,652 | 12/1971 | Fujimoto et al. ............ | 436/178 |
| 3,668,936 | 6/1972 | Herron ......................... | 73/864.22 |
| 3,879,127 | 4/1975 | Storr et al. .................. | 210/656 X |
| 4,054,648 | 10/1977 | Nagasawa et al. .......... | 424/105 |
| 4,070,284 | 1/1978 | Fujita et al. ................. | 436/161 X |
| 4,108,608 | 8/1978 | Maher, Jr. et al. .......... | 422/100 X |
| 4,137,307 | 1/1979 | Funakoshi et al. .......... | 424/177 |
| 4,267,056 | 5/1981 | McClure ...................... | 436/178 X |
| 4,269,708 | 5/1981 | Bonomini et al. ........... | 210/254 X |
| 4,444,661 | 4/1984 | Jackson et al. .............. | 210/446 |
| 4,528,158 | 7/1985 | Gilles et al. .................. | 436/180 X |

FOREIGN PATENT DOCUMENTS

| | | |
|---|---|---|
| 54-150195 | 11/1979 | Japan .................................. 436/161 |
| 1530847 | 11/1978 | United Kingdom . |
| 1581353 | 12/1980 | United Kingdom . |
| 1581354 | 12/1980 | United Kingdom . |

OTHER PUBLICATIONS

Burns, Donald A.; Fast–LC Concepts for Automated Pesticide Analysis; Pesticide Analytical Methodology; ACS Symposium Series 136; Washington, D.C., 1980.
Mohammed et al, Chemical Abstracts, vol. 96, Abstract No. 96:65079j, 1981.
Knudson et al, Clin. Chem., vol. 24, No. 4, pp. 686–691, 1978.
Mohammed et al, J. of Chromatography, vol. 226, pp. 471–476 (1981).

*Primary Examiner*—Robert J. Hill, Jr.
*Attorney, Agent, or Firm*—Nixon & Vanderhye

[57] ABSTRACT

A plurality of analytes are analyzed by liquid chromatography in a liquid biological sample containing many components which can interfere with analysis by liquid chromatography. The sample, containing the analytes of interest, are passed to a first passage of a dialyzer which removes molecules in the sample which interfere with analysis. A diluent is passed through a second passage of the dialyzer in which the two liquids are separated from each other by a semipermeable membrane having holes large enough to permit the analytes of interest to pass into the diluent but holes small enough to prevent passage of sample components which interfere with analysis. The analyte-containing diluent is passed to a retaining element for temporarily retaining the analytes of interest by adsorption and/or partition. The analytes of interest are removed from the retaining element by a second diluent which is then passed through a chromatography column with a detector and the analytes are analyzed chromatographically. The portion of the sample containing the interfering molecules is discarded.

10 Claims, 6 Drawing Sheets

SAMPLE PREPARATION METHOD FOR LIQUID CHROMATOGRAPHY

This invention relates to a method of and an apparatus for preparing a sample for analysis by liquid chromatography. The invention also relates to an element for retaining components of a sample liquid and further to a probe for mixing liquids.

When it is desired to use liquid chromatography to analyze a sample of a complex nature such as a biological sample, preparation is necessary to remove compounds which might otherwise interfere with the analysis. Hitherto, such samples have been prepared by mixing them with a suitable reagent such as an acid and then separating the unwanted compounds from the remainder of the sample in a centrifuge. This method of preparation is difficult to perform and does not always provide satisfactory results. Moreover, preparation by such a method may be lengthy which can cause problems where labile derivatives are formed. A further disadvantage is that this method cannot be readily automated.

It is an object of this invention to provide a new or improved method of preparing samples for analysis by liquid chromatography which does not suffer from the above-mentioned disadvantages and it is a further object to provide an apparatus for performing the method.

According to one aspect of this invention there is provided a method of preparing a sample for analysis by liquid chromatography comprising passing the sample through a first passage in a dialyzer, passing a diluent through a second passage in the dialyzer, the first and second passages being separated by a semi-permeable membrane so that components of the sample pass through the membrane into the diluent, and passing the diluent which contains components of the sample through a passage in an element which contains material for retaining said components of the sample.

In the method of this invention, the wanted components are separated from the remainder of the sample in the dialyzer and these wanted components are then retained in concentrated form in the sample retaining element. They may then be removed for analysis by passisng a solvent through the element and so the prepared sample may be analyzed immediately. This method may be readily automated.

According to another aspect of this invention, there is provided an apparatus for preparing samples for analysis by liquid chromatography comprising a dialyzer having a first passage and a second passage which is separated from the first passage by a semi-permeable membrance and an element having a passage which contains material for retaining components of the sample, the inlet of the first passage of the dialyzer being connected to a tube for receiving the sample, the inlet of the second passage of the dialyzer being connected to a tube for receiving diluent and the outlet of the second passage being connectable to the inlet of the passage in the sample retaining element.

It is a further object of this invention to provide an element for retaining components of a liquid sample passing therethrough.

According to a further aspect of this invention there is provided an element for retaining components of a liquid sample passing therethrough, said element comprising a pair of members detachably connected together and a disposable cartridge positioned in a well formed inside the element, each of said members having a passage formed therein which communicates with the well.

It is yet another aspect of this invention to provide a probe for mixing a sample liquid with a diluent.

Acording to a still further aspect of this invention there is provided a probe for mixing a sample liquid with a diluent comprising a passage extending between a first inlet for receiving the sample liquid and a second inlet for receiving the diluent, and a tube, part of said tube being located inside the passage, one end of said tube being located adjacent to the first inlet and the other end of said tube providing the outlet of the probe.

BRIEF DESCRIPTION OF THE DRAWINGS

This invention will now be described in more detail, by way of example, with reference to the accompanying drawings, in which:

Referring now to FIG. 1, there is shown a high pressure liquid chromatography apparatus comprising a solvent reservoir 10 which is connected through a tube 11 to the inlet of a high pressure pump 12. The outlet of pump 12 is connected through a tube 13 to an inlet 14a of a six port injection valve 14. Port 14b of valve 14 is connected through a tube 15 to the inlet of analytical column 16 which contains material such as modified silica for separating the components of the sample to be analysed. The column 16 may be an ALTEX 420 150 mm×4.6 mm internal diameter column prepacked with 5 micrometer diameter Ultrasphere ODS (Anachem Ltd., Luton, U.K.). The outlet of the column 16 is connected through a tube 17 to the inlet of a detector 18, the outlet of which is connected to waste. The detector 18 is connected to a recorder 19. The detector 18 may be a Schoeffel FS 970 fluorescence detector (Kratos, Manchester, U.K.). Ports 14c and 14d of valve 14 are connected to a loop 20, port 14e is connected to a tube 21 for receiving the sample to be analysed and port 14f is connected to waste.

Figure 1:
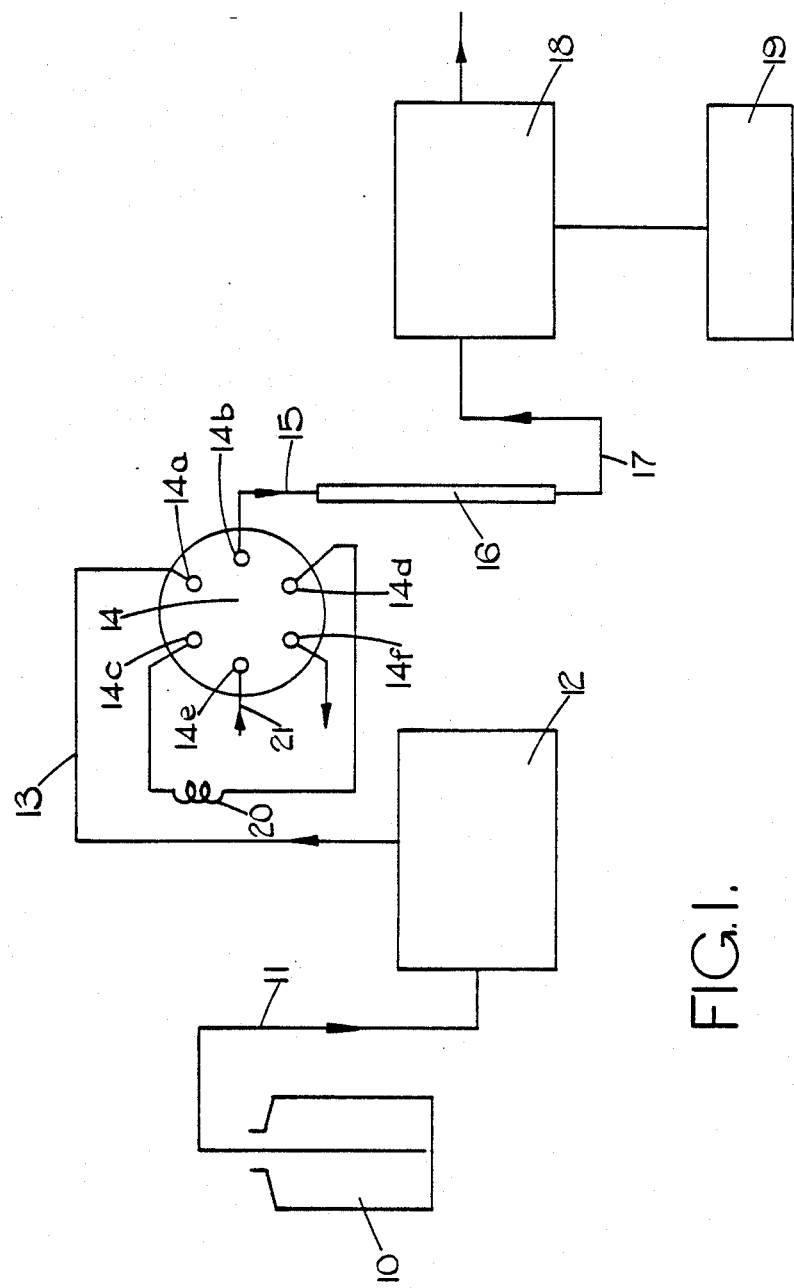
FIG. 1 shows in diagrammatic form a conventional liquid chromatography apparatus.

In operation, the ports 14e, 14c, 14d and 14f of valve 14 are connected in series and the sample to be analysed is drawn into the loop 20. At the same time, ports 14a and 14b are connected together so that pure solvent passes through the column 16. Then, ports 14a, 14c, 14d and 14b are connected in series and the sample is injected into the solvent stream, the components are separated in the column 16 and analysed in the detector 18 and a chromatogram is produced on the recorder 19.

Figure 2:
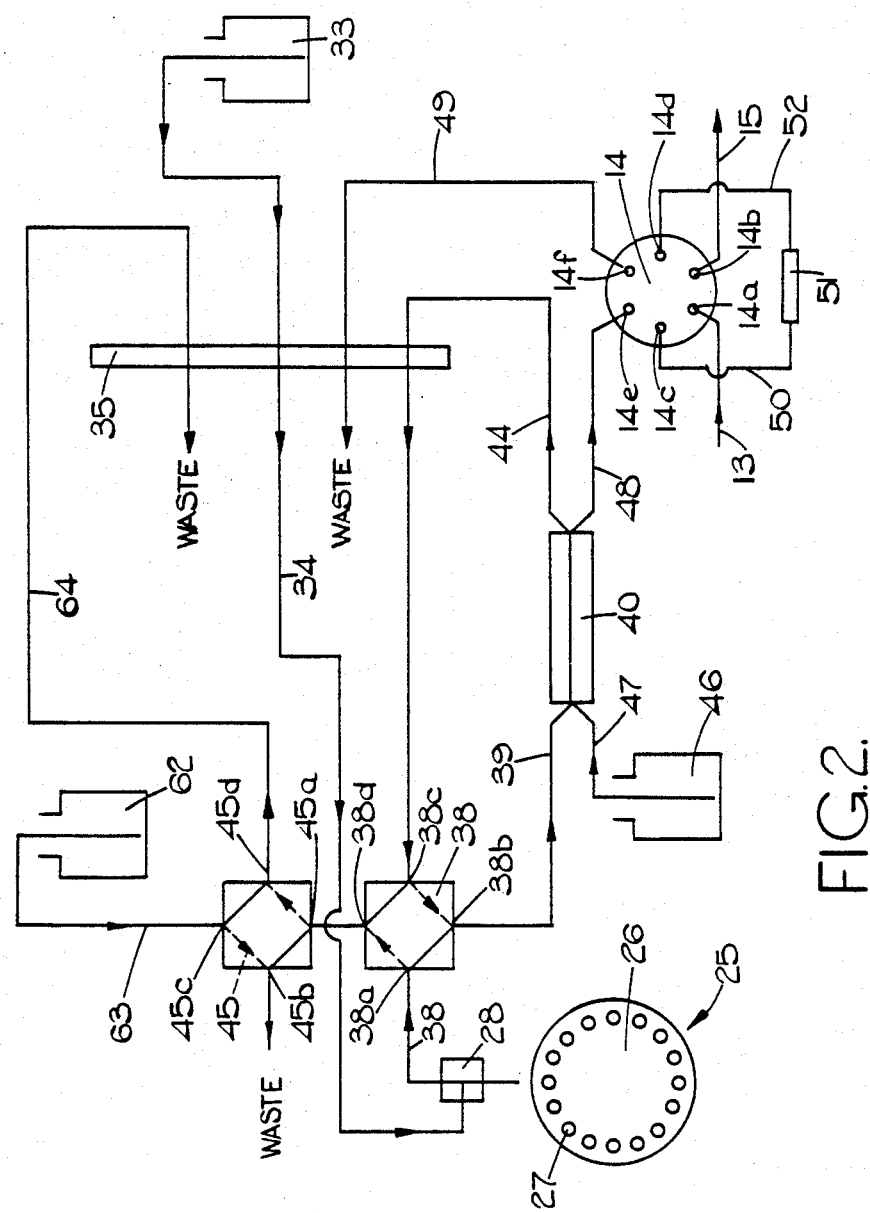
FIG. 2 shows in diagrammatic form an apparatus for preparing samples for analysis by liquid chromatography.

The apparatus shown in FIG. 1 may be used either with samples which do not require preparation or which have been prepared prior to analysis. In FIG. 2, there is shown an apparatus for preparing samples such as those of a biological nature which contain compounds which need to be eliminated prior to analysis and which may be connected to the apparatus shown in FIG. 1 in place of the loop 20 and the tube 21.

Referring now to FIG. 2, the apparatus thereshown, includes a sampler 25 which comprises a rotary plate 26 provided with cups 27 for holding samples to be analysed. The sampler 25 also has a wash reservoir (not shown). The sampler 25 may be a Technicon Auto Analyser 2 obtained from Technicon Instruments Corporation, Tarrytown, N.Y., U.S.A. The sampler 25 is associated with a probe 28 which is shown in more detail in FIG. 3A in operation removing a sample from one of the cups 27. The probe 28 has a tube in the form of a steel needle 70 mounted in a bore 71 in a perspex block 72. The needle 70 has an inlet 73. A thin steel tube 74 is mounted with epoxy cement 85 inside the bore 71 and extends from inlet 73 to a position beyond the block 72, the free end of the tube 74 outside tube 70 forming the outlet 78 of the probe. A further steel tube 75 of internal diameter approximately equal to that of needle 70 is mounted inside a bore 76 which intersects the bore 71. The free end of tube 75 forms an inlet 77 for receiving diluent and the needle 70. bores 71 and 76 and tube 75 together define a passage which extends from inlet 77 to inlet 73. By arranging that the flow rate at outlet 78 is greater than the flow rate at inlet 77, a sample will be drawn in at inlet 73, and, as the sample and diluent mix at the entrance to tube 74, precise mixing may be achieved. The inlet 77 receives diluent from a reservoir 33 moved through a tube 34 by a peristaltic pump 35. The pump 35 is a Technicon Auto Analyser 1 peristaltic pump. With this particular pump, in order to ensure precise mixing, the ration of the flow rate at outlet 78 to the flow rate at inlet 77 should be three. The diluent may take the form of a solvent or a reagent. If it is desired to use two reagents, the probe may be modified as shown diagrammatically in FIG. 3B. In FIG. 3B, the probe has a further inlet 79 which is connected to an opening 80 in tube 74 through a passage 81. The passage 81 is separated from the tube 75 by a stopper 82. If desired, small heating coils may be provided in tube 75 or passage 81.

Figure 4A:
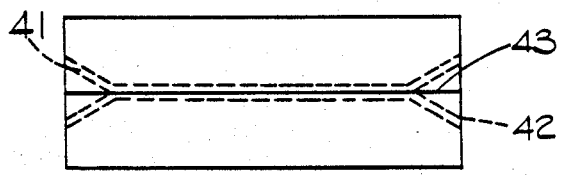
FIG. 4A is an elevational view of a dialyzer forming part of the apparatus of FIG. 2A.
Figure 4B:
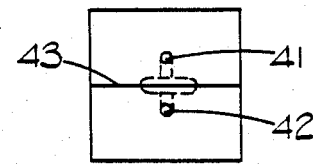
FIG. 4B is an end view of the dialyzer.
Figure 4C:
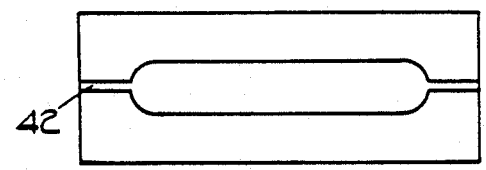
FIG. 4C is a view of the bottom half of the dialyzer with its membrane removed.

The outlet of the probe 28 is connected through a tube 29 to a port 38a of a four port valve 38. A port 38b of valve 38 is connected through a tube 39, to the inlet of a first passage of a dialyzer 40. The dialyzer 40 is shown in more detail in FIGS. 4A, 4B and 4C and as there shown comprises first and second passages 41, 42 which are separated by a semi-permeable membrane 43. The dialyzer is arranged so that the membrane presents a large surface area to the fluids flowing through the passages 41 and 42 in relation to the volume of these passages. The inlets and outlets of passages 41 and 42 are shaped to minimize flow turbulence. The membrane is selected so that its holes are sufficiently large to permit passage of the molecules of those components of the sample which it is desired to analyze and sufficiently small to prevent passage of those molecules which interfere with the analysis. The membrane may be made from material sold under the trade name CUPROPHANE.

In order to minimize the required volume of the sample, the dialiyzer 40 should be small and its length may, for example, be in the range 25 to 75 mm.

The outlet of the first passage 41 of dialyser 40 is connected through a tube 44 which passes through the peristaltic pump 35 to a port 38c of valve 38. A port 38d of this valve is connected to a port 45a of a four port valve 45 and a port 45b of this valve is connected to waste. The four port valves 38 and 45 and the valve 14, may be obtained from Anachem Limited, 15 Power Court, Luton.

A diluent reservoir 46 is connected through a tube 47 to the inlet of passage 42 and the outlet of passage 42 is connected through a tube 48 to port 14e of valve 14. Port 14f is connected through the tube 49 which passes through the pump 35 to waste. The diluent in reservior 46 may be a solvent or a reagent.

Figure 5:
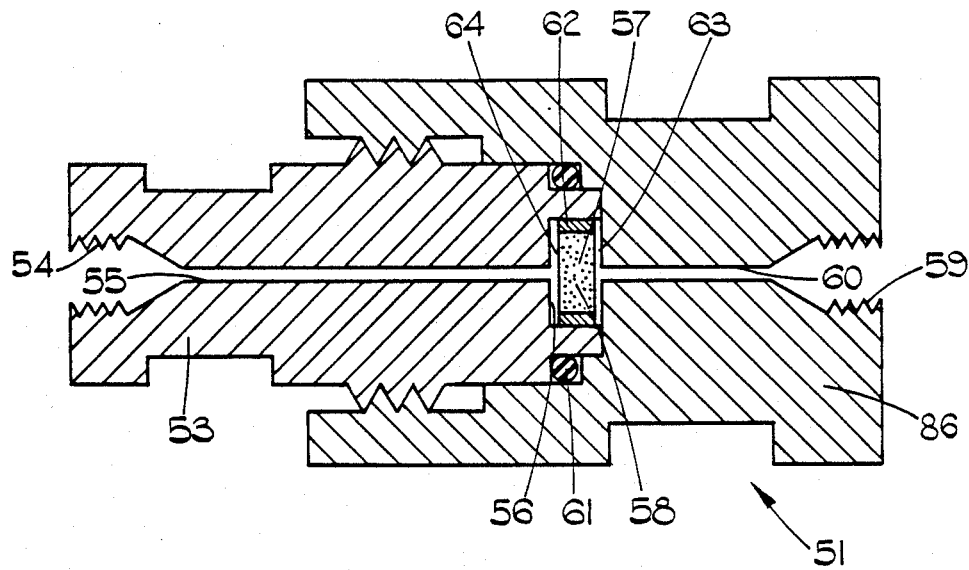
FIG. 5 is a sectional view of an element which forms part of the apparatus of FIG. 2.

Port 14c of valve 14 is connected through a tube 50 to the inlet of an element 51 for retaining desired components of the sample and the outlet of this element is connected through a tube 52 to port 14d. As shown in more detail in FIG. 5, the element 51 comprises a first member 53 which has an internal screw thread 54 for connection to the pipe 50 and which leads to a passage 55 of circular cross-section. At the other end, the passage 55 leads to a well 56 which contains a cartridge 57 provided with material 58 for retaining components of the sample. The cartridge 57 comprises a steel ring 62 and a steel mesh 63 and a nylon mesh 64 which together define a space which encloses the material 58. The member 53 is threadedly connected to a second member 86 which has an internal screw thread 59 for connection to the tube 52 leading to a passage of circular cross-section 60. An O-ring 61 is provided in a groove between the members 53 and 86. The cartridge 57 may be removed simply be unscrewing members 53 and 86. The material 58 retains components by adsorption or partition or by a mixture of these two mechanisms. In order to minimize the required volume of the sample, the element 51 should be small and, for example its length may be about 25 mm.

Finally, a water reservoir 62 is connected through a tube 63 to a port 45c of valve 45 and port 45d of this valve is connected through a tube 64 through the pump 35 to waste.

Figure 6:
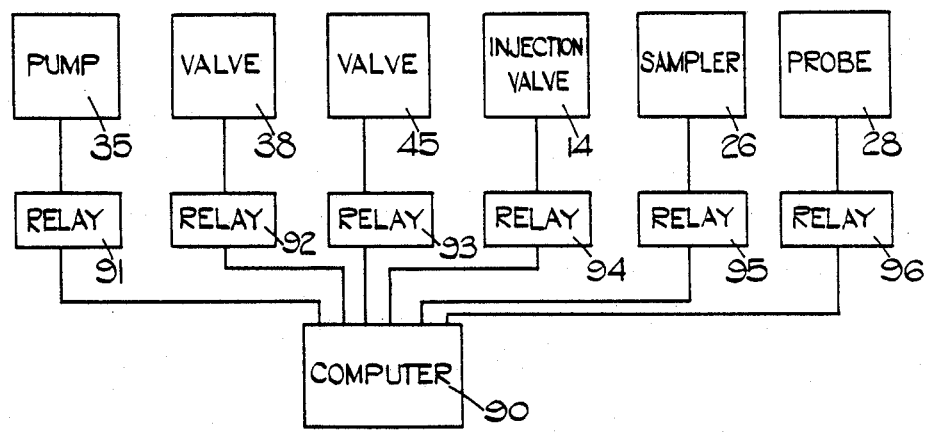
FIG. 6 is a block diagram showing the electrical connections between parts of the apparatus of FIG. 2.

The apparatus shown in FIG. 2 may be controlled automatically and one arrangement for doing this is shown in FIG. 6. As there shown, the pump 35, valves 38, 45 and 14, the sampler 25 and probe 28 are operated by a computer 90 through relays 91 to 96. The computer 90 may be a SP4100 computing integrator made by Spectra-Physics Ltd., St. Albans, U.K. When using the computing integrator, external connections $T_3$ to $T_8$ are used to drive relays 91 to 96. The computing integrator also serves as recorder 19 shown in FIG. 1.

Figure 7:
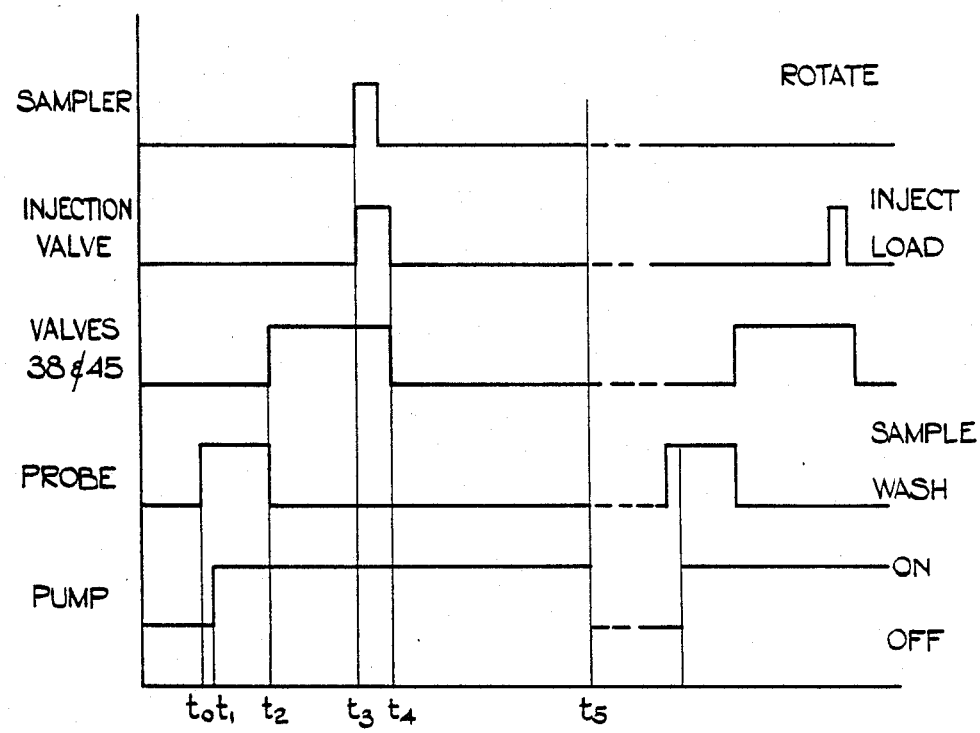
FIG. 7 is a timing diagram illustrating the operation of the apparatus of FIG. 2.

The operation of the apparatus will now be described with reference to FIG. 7. At time $t_0$, probe 28 is transferred from the wash reservoir into one of the sampler cups 27. At time $t_1$, the pump 35 is energized. At this time, the valves 38 and 45 occupy the positions shown by solid lines and the valve 14 is positioned so that ports 14e, 14c, 14d and 14f are connected in series. The sample is then mixed with the diluent from reservoir 33. At time $t_2$ which is just before the resulting mixture reaches port 38c of valve 38, the probe is transferred back into the wash reservoir and the valves 38 and 45 are moved into the position shown by dashed lines. The mixture of diluent and sample then circulates through tubes 39 and 44 passing through passage 41 of the dialyser 40 whilst fresh diluent from the reservoir 46 passes through the passage 42 and then through element 51 to waste. The components of the sample which are to be analysed will be of small molecular size and so these will pass through the membrane 43 into the diluent from reservoir 46 and they are then selectively retained in the material 58 in element 51. By continuing the circulation for a sufficiently long period all the components of interest will be extraced from the remainder of the sample and concentrated in element 51.

In order to perform the analysis, at time $t_3$, the valve 14 is operated so that ports 14a, 14c, 14d and 14b are connected in series and the components from the sample are injected into the solvent from reservoir 10 shown in FIG. 1 for separation in column 16 and analysis in the detector 18. Also, at time $t_3$ the sampler 26 is operated so as to bring the next cup 27 into position beneath probe 28. At time $t_4$ valves 38, 45 and 14 are returned to their first position. At time $t_5$ the pump 35 is switched off. When the chromatography analysis has been completed, the cycle may be repeated with the next sample.

As mentioned above, the diluent in reservoir 33 and 46 may be solvent or a reagent. Where no chemical modification is required a suitable solvent is used in both reservoirs. For example, when analyzing samples of a biological nature such as blood, urine or foodstuffs the solvent may be a salt solution or an alcohol.

Reagents may be used when it is desired to assist dialysis in dialyser 40 or adsorption or partition in element 51. Where the analyte is an acid, dialysis, adsorption and partition will be assisted by using a stronger acid as the reagent and where the analyte is an alkali such assistance will be achieved by using a stronger alkali as the reagent. Where the analyte has a high polarity dialysis, adsorption and partition may be assisted by using an organic solvent such as pentanol or by increasing the ionic strength and this may be achieved by using ammonium sulphate. Dialysis may also be improved by using a chelating agent such as EDTA in reservoir 46.

By way of example, when analyzing an anti-convulsant drug such as phenobarbitone in a blood sample, the reagent in both reservoirs 33 and 46 may be a weak acetate buffer. Phenabarbitone is a weak acid and so the weak acetate buffer will assist dialysis, adsorption and partition.

Reagent may also be used to form derivatives which assist the chromographic analysis. For example, when analysing amino acids in blood, iodoacetic acid can be used in reservoir 33 to derivatize cysteine and OPA (orth0-pthaladehyde) is used in reservoir 46 to form flourescent derivatives of amino acids. Reagents which form derivatives may be used on their own or together with reagents which assist dialysis, partition and adsorption.

As mentioned above, the components of interest are retained in the material 58 in element 51 by adsorption, partition, or both of these mechanisms. Where it is desired to use only adsorption, unmodified silica crystals may be used and, where it is desired to use both adsorption and partition, silica crystals which have been subjected to reaction with ODS (ocladecyl silane) may be used. Adsorption may also be achieved by anion or cation exchange by using, for example, suitably modified silica crystals. Silica crystals for achieving adsorption, a mixture of adsorption and partition, adsorption by cation exchange, and adsorption by anion exchange are manufactured by Whatman Chemical Separation Limited under their respective trade names Co-Pell PAC, Co-Pell ODS, Co-Pell SCX, and Co-Pell SAX.

Figure 8:
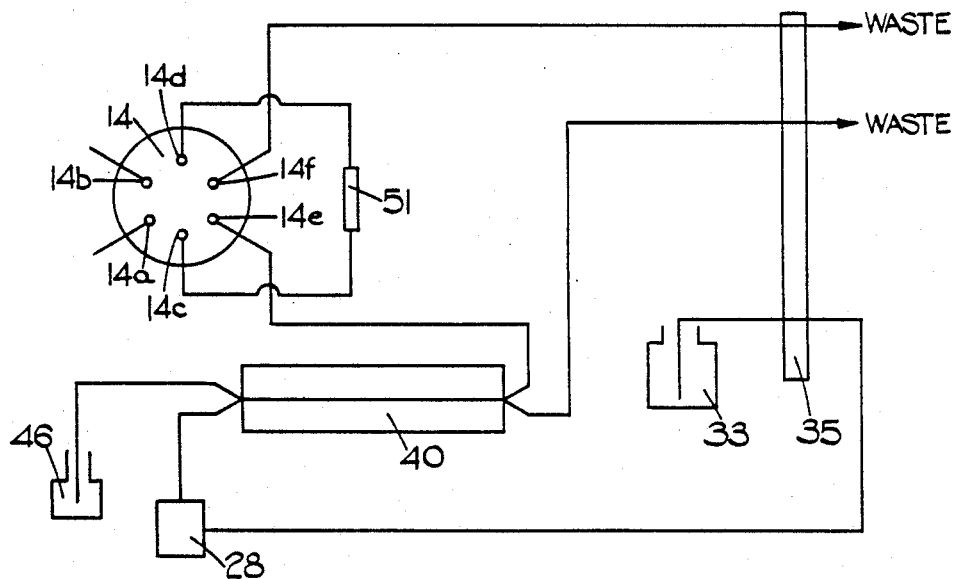
FIG. 8 shows in diagrammatic form another apparatus for preparing samples.

An alternative arrangement for preparing samples for analysis is shown in FIG. 8, where like parts are denoted by the same reference numerals as in FIG. 2. In the arrangement of FIG. 8, valves 38 and 45 are not used. In operation, the pump 35 is switched on until the sample is located in dialyser 40 and the pump is then turned off whilst dialysis proceeds. After a suitable interval, for example one minute, the pump is again turned on thereby loading element 51 with the components of interest. Whilst this arrangement does not achieve exhaustive dialysis, it does permit analysis of very small samples.

Figure 3A:
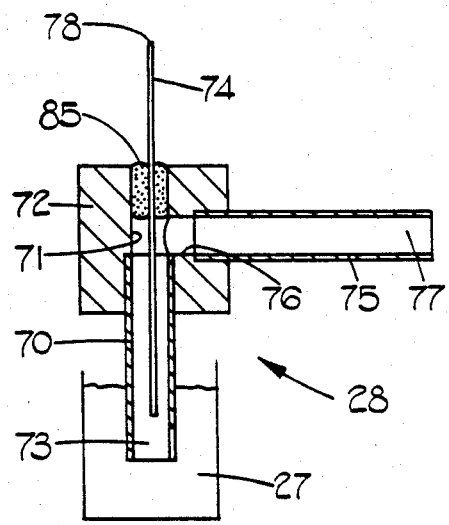
FIG. 3A is a sectional view of a probe which forms part of the apparatus shown in FIG. 2.
Figure 3B:
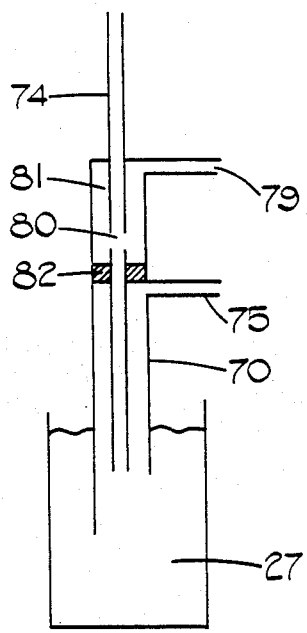
FIG. 3B is a diagram illustrating a modification to the probe of FIG. 3A.
Figure 9:
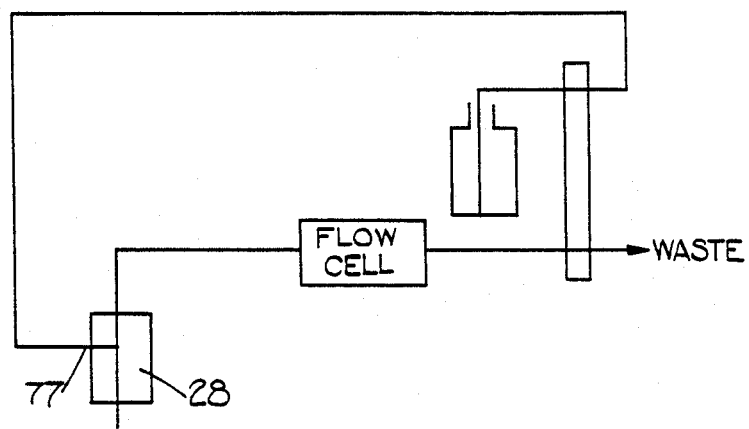
FIG. 9 shows in diagrammatic form an apparatus for performing flow injection analysis.

The probes shown in FIGS. 3A and 3B may be used in other applications where precise mixing is required. In FIG. 9 there is shown an example of probe 28 being used for flow injection analysis. In this example, diluent is supplied from a reservoir 100 through a pump 101 to inlet 77 of the probe 28. The outlet of the probe is connected to the inlet of a flow cell 102, the outlet of which is connected through pump 101 to waste. When it is desired to analyze a sample, probe 28 is lowered into the sample and pump 101 is energized.

We claim:

1. A method of selectively analyzing a plurality of analytes in a liquid biological sample containing many components which can interfere with analysis by liquid chromatography, said method comprising the steps of:
    (a) passing a biological liquid sample containing a plurality of analytes of interest and molecules which can interfere with analysis by liquid chromatography into a first passage of a dialyzer;
    (b) selectively removing the molecules in the sample which can interfere with analysis by liquid chromatography from the analytes of interest by passing a first diluent through a second passage of the dialyzer, the first and second passages being separated by a semipermeable membrane having holes sufficiently large to permit the analytes of interest to pass through the membrane into the first diluent but sufficiently small to prevent passage of the molecules which can interfere with analysis by liquid chromatography, and passing the analytes of interest from the sample, through the membrane, and into the first diluent to form a dialyzed sample which still contains the molecules which can interfere with analysis by liquid chromatography;
    (c) passing the first diluent containing the analytes of interest through a passage in a retaining element which contains material for temporarily retaining the analytes of interest by either adsorption, partition or both;
    (d) subsequently passing a second diluent through the passage in the retaining element in order to remove the analytes of interest;
    (e) passing the second diluent containing the analytes of interest through a chromatography column and detector means in order to perform chromatographic analysis of the analytes of interest; and
    (f) passing the dialyzed sample which contains the molecules which can interfere with analysis by liquid chromatography to waste.

2. The method as claimed in claim 1, in which the sample is circulated repeatedly through the first passage of the dialyzer while fresh first diluent is passed through the second passage.

3. The method as claimed in claim 1, in which the biological sample is blood.

4. The method as claimed in claim 3, in which amino acids in the blood are analyzed.

5. The method as claimed in claim 3, in which the blood is analyzed for an anti-convulsant drug.

6. The method as claimed in claim 1, in which the biological sample is urine.

7. The method as claimed in claim 1, in which the biological sample is a foodstuff.

8. The method as claimed in claim 1, in which the sample is held stationary in the first passage of the dialyzer while passing the analytes of interest through the membrane into the first diluent.

9. The method as claimed in claim 1, comprising the additional step of mixing the sample with a third diluent prior to passing the sample into the first passage of the dialyzer.

10. The method as claimed in claim 9, in which the third diluent is a reagent.

* * * * *